United States Patent
Sasaki et al.

(10) Patent No.: US 6,168,939 B1
(45) Date of Patent: Jan. 2, 2001

(54) ENDOPEPTIDASE PRODUCED BY LACTOBACILLUS HELVETICUS

(76) Inventors: Masahiro Sasaki, Anemoonweg 44, 9765 HG, Paterswolde; Boukje Bosman, Broekstukken 25, 9761 KD, Eelde; Paris S. T. Tan, Emdaborg 14, 9751 SJ, Haren, all of (NL); Shin'ichi Takafuji, 62-32, Kotsuzumi, Kawagoe, Saitama-Shi (JP); Taisuke Iwasaki, Hemsterhuislaan 17, 9752 NA, Haren (NL)

( * ) Notice: Under 35 U.S.C. 154(b), the term of this patent shall be extended for 0 days.

(21) Appl. No.: 08/611,395

(22) Filed: Mar. 6, 1996

(30) Foreign Application Priority Data

| Mar. 7, 1995 | (JP) | 7-74650 |
| Aug. 30, 1995 | (JP) | 7-245307 |

(51) Int. Cl.$^7$ ................................ C12N 9/50
(52) U.S. Cl. .................... 435/219; 435/183; 435/70.1
(58) Field of Search ............... 435/219, 183, 435/70.1

(56) References Cited

U.S. PATENT DOCUMENTS

| 4,515,891 | 5/1985 | Yokogawa et al. ............... 435/69 |

FOREIGN PATENT DOCUMENTS

| 0 406 598 B1 | 1/1991 | (EP) | A23J 3/34 |
| 0522203 A1 | 1/1993 | (EP) | C12N 9/52 |
| 0 633 316 A1 | 1/1995 | (EP) | C12N 15/57 |
| WO 94/16082 | 7/1994 | (WO) | C12N 15/57 |
| WO 94/26882 | 11/1994 | (WO) | C12N 9/48 |

OTHER PUBLICATIONS

K.M. Fenster et al., "Cloning of Endopeptidases from *Lactobacillus Helveticus* CNRZ32", *Journal of Animal Science* 72(1), Annual Meeting Abstract of the Combined Teaching of the American Diary Science Association and the American Society of Animal Science, Minneapolis, MN, July 11–15, 1996.

C.M. Nowakowski et al., "Cloning of Peptidase Genes from *Lactobacillus Helveticus* CNRZ32" *Applied Microbiology and Biotechnology* 39:204–210 (1993).

F. Prost et al., "Effect of Aminopeptidase Activity of Thermophillic Lactobacilli Emmental Cheese Characteristics", *J. Dairy Sci.* 77(1):24–33 (1994).

M. Sasaki et al., "Comparison of Proteolytic Activities in Various Latobacilli", *J. Dairy Res.* 62:601–610 (1995).

P.S.T. Tan et al., "Purification and Characterization of a Dipeptidase from *Lactobacillus helveticus* SBT 2171", *Appl. and Environ. Microbiology* 61(9):3430–3435 (1995).

H. Cholette et al., "Influence of pH on the Properties of *Lactobacillus helveticus* Aminopeptidase", *J. Diary Sci.* 73(9):2278–2286 (1990).

N. Ezzat et al., "Cell–Wall Associated Peptide Hydrolase and Esterase Activities in Several Cheese–Related Bacteria", *Food Chemistry* 48:19–23 (1993).

D.H. Hemme et al., "Effect of the Addition of Extracts of Thermophilic Lactobacilli on Acid Production by *Steptococcus Thermophilus* in Milk" *J. Dairy Res.* 48(1):139–148 (1981).

N.M. Khalid et al., "Peptide Hydrolases of *Lactobacillus helveticus* and *Lactobacillus delbrueckii* ssp. *bulgaricus*", *J. Dairy Sci.* 74(1):29–45 (1991).

J. Kok et al., "Genetic Manipulation of the Peptidolytic SYstem in Lactic Acid Bacteria", *Intl. Dairy Journal* 5:737–755 (1995).

H. Kataoka et al. "Determination of Glutathrone and Related Aminothiols by Gas Chromatography with Flames Photometric Detection" *Biomed. Chromatography* 9(2):85–89 (1995).

H. Miyakawa et al., "Purification and Characterization of an Aminopeptidase from *Lactobacillus helveticus* LHE–511", *J. Dairy Sci.* 75(1):27–35 (1992).

H. Miyakawa et al., "Purification and Characterization of a Prolyl Aminopeptidase from *Lactobacillus helveticus* LHE–511", *Milk Science Intl.* 49(11):615–619 (1994).

H. Miyakawa et al., "Purification and Characterization of an X–Prolyl Dipeptidyl Aminopeptidase from *Lactobacillus helveticus* LHE–511" *Milk Science Intl.* 49(12):670–673 (1994).

*Primary Examiner*—Leon B. Lankford, Jr.

(57) ABSTRACT

An endopeptidase produced by *Lactobacillus helveticus* which hydrolyzes peptides with about 3–34 amino acid residues, but not proteins, has been discovered. The enzyme has a molecular weight of about 70 kDa, an isoelectric point of about 4.8, an optimal temperature of about 30° C. and an optimal pH of about 7.0. No homologous endopeptidase was found in a data base search of the N-terminal amino acid sequence of the enzyme, and thus the enzyme is novel. The endopeptidase can be used together with proteolytic enzymes such as proteinases and aminopeptidases using the substrate specificity of the endopeptidase to effectively degrade proteins. The endopeptidase can be applied singly to selectively produced specific peptides. The protein hydrolysate can be used for the preparation of foods, drinks and medicines.

5 Claims, 4 Drawing Sheets

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 26 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 1:

```
Val Arg Gly Gly Ala Gly Asp Ile Thr Glu Ala Asp Leu Ser Ala Ar
1               5                   10                  15

Pro Gln Asp Asn Leu Tyr Leu Ala Val Asn
            20                  25
```

(2) INFORMATION FOR SEQ ID NO: 2:

(i) SEQUENCE CHARACTERISTICS:
      (A) LENGTH: 5 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 2:

```
Tyr Gly Gly Phe Met
1               5
```

(2) INFORMATION FOR SEQ ID NO: 3:

(i) SEQUENCE CHARACTERISTICS:
      (A) LENGTH: 4 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 3:

```
Ala Ala Ala Ala
1
```

(2) INFORMATION FOR SEQ ID NO: 4:

(i) SEQUENCE CHARACTERISTICS:
      (A) LENGTH: 4 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 4:

```
Gly Pro Gly Gly
1
```

(2) INFORMATION FOR SEQ ID NO: 5:

(i) SEQUENCE CHARACTERISTICS:
      (A) LENGTH: 4 amino acids

```
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

Gly Pro Arg Pro
1

(2) INFORMATION FOR SEQ ID NO: 6:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

Pro Lys Gly Gly
1

(2) INFORMATION FOR SEQ ID NO: 7:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 7:

Ala Ala Ala Ala Ala
1               5

(2) INFORMATION FOR SEQ ID NO: 8:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 8:

Pro Gly Lys Ala Arg
1               5

(2) INFORMATION FOR SEQ ID NO: 9:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 9:

Ala Ala Ala Ala Ala Ala
1               5

(2) INFORMATION FOR SEQ ID NO: 10:

(i) SEQUENCE CHARACTERISTICS:
```

```
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Suc-Ala"

(ix) FEATURE:
        (A) NAME/KEY: Modified-site
        (B) LOCATION: 4
        (D) OTHER INFORMATION: /product= "Leu-pNA"

(xi) SEQUENCE DESCRIPTION: SEQ ID NO: 10:

Xaa Ala Pro Xaa
```

ENDOPEPTIDASE PRODUCED BY *LACTOBACILLUS HELVETICUS*

FIELD OF THE INVENTION

This invention relates to a novel endopeptidase produced from the culture of *Lactobacillus helveticus*. The endopeptidase of the present invention does not degrade proteins but degrades peptides, and thus can be used together with other proteolytic enzymes such as proteinases and aminopeptidases to effectively produce protein hydrolysate used for foods and drinks, and medicines. In addition, the endopeptidase of the present invention can be used solely to selectively produce specific peptides.

BACKGROUND OF THE INVENTION

Heretofore, a number of proteolytic enzymes derived from various sources are known, and they have been utilized in various fields. Among them, proteolytic enzymes derived from lactococci have been used in food processing industries because of their safety. In particularly, endopeptidases derived from lactococci hydrolyze large peptides generated by the action of proteinases on proteins and are deemed to be very important enzymes for the effective degradation of proteins. For example, an endopeptidase produced by *Lactococcus lactis* ssp, cremoris was purified and its properties are well elucidated [Japanese Laid-open (KOKAI) Patent Application No. 268955 (1993)].

However, purified endopeptidase has heretofor not been obtained from *Lactobacillus helveticus*, a lactobacillus which is used to ferment dairy products such as fermented milk and cheese and plays an important role in industrial fields, particularly the food industry.

The inventors of the present invention have found a novel endopeptidase produced by *Lactobacillus helveticus* which specifically hydrolyzes peptides by attacking peptide bonds within peptide without hydrolyzing proteins such as various caseins.

SUMMARY OF THE INVENTION

One object of the present invention is to provide an endopeptidase which produced by *Lactobacillus helveticus*, specifically hydrolyzes peptides having the following physicochemical properties:

(1) a molecular weight of about 70 kDa, as determined by SDS polyacrylamide gel electrophoresis;

(2) an isoelectric point of about 4.8;

(3) an optimal temperature of about 30° C.;

(4) an optimal pH of about 7.0; a Michaelis constant ($K_m$ value) of about 0.20 mM and a maximum velocity ($V_{max}$ value) of about 56 μmol/min./mg by hydrolysis of the substrate Tyr-Gly-Gly-Phe-Met;

(6) substrate specificity whereby the endopeptidase attacks peptide bonds inside peptides to hydrolyze the peptides without hydrolyzing proteins;

(7) it is inhibited by the enzyme inhibitors 1,10-phenanthroline, ethylenediaminetetra-acetic acid (EDTA), and p-chloromercuribenzenesulfonic acid (p-CMBS).

(8) the endopeptidase's activity is inhibited by $Cu^{2+}$, $Zn^{2+}$, and $Fe^{2+}$.

The endopeptidase of the present invention does not react with a polyclonal antibody raised against an endopeptidase produced by *Lactococcus lactis* ssp. cremoris Wg2 strain of the lactic acid-forming coccus. Thus the endopeptidase of the present invention is immunologically different from that produced by the Wg2 strain.

Furthermore, the amino acid sequence of the N-terminus of the endopeptidase of the present invention is Val-Arg-Gly-Gly-Ala-Gly-Asp-Ile-Thr-Glu-Ala-Asp-Leu-Ser-Ala-Arg-Pro-Gln-Asp-Asn-Leu-Tyr-Leu-Ala-Val-Asn- (SEQ ID NO:2). The homology of the sequence to data bases of all proteins and DNAs was searched in the literature and using a BLAST program, but no homologous or nearly homologous enzyme was found. Thus the enzyme of the present invention is considered as a novel enzyme.

DETAILED DESCRIPTION OF THE INVENTION AND PREFERRED EMBODIMENTS

Figure 1:
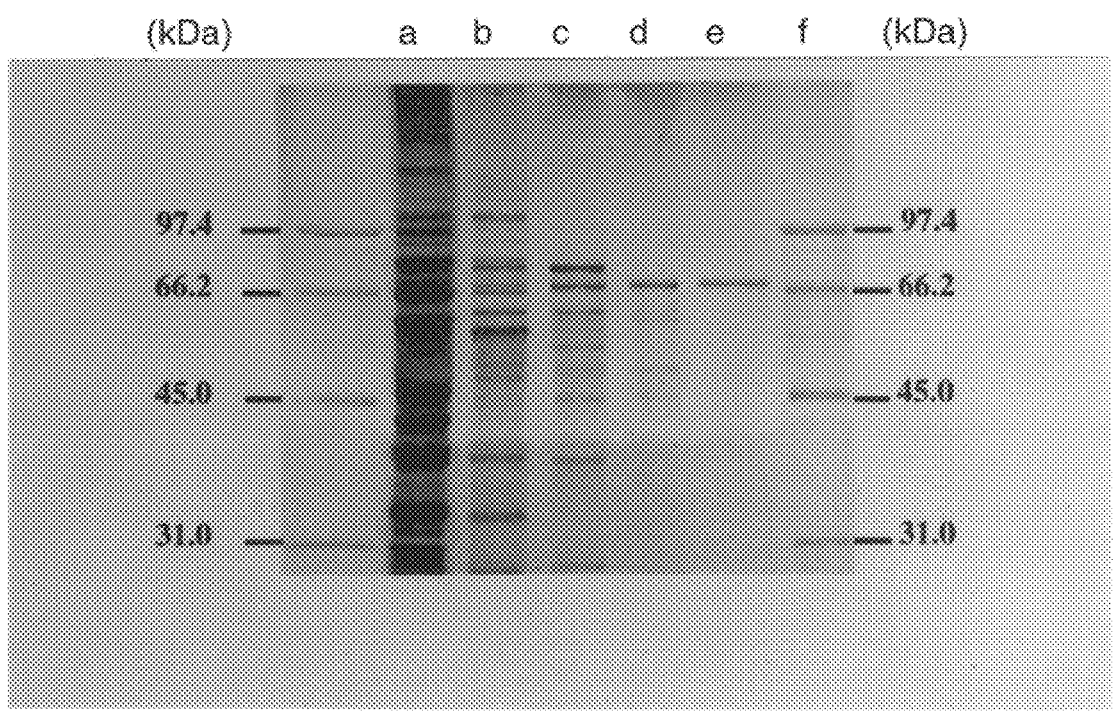
FIG. 1 shows the patterns of SDS polyacrylamide gel electrophoreses of the endopeptidase of the present invention during purification steps according to Example 2.

The endopeptidase of the present invention can be obtained by culturing *Lactobacillus helveticus* by conventional culturing methods, harvest of cultured cells, disruption of harvested cells, and purification of the enzyme by conventional purification methods.

The strain which produce the endopeptidase of the present invention can be obtained from fermented milk in market by the following procedure. At first, one gram of a fermented milk was suspended in a sterilized saline and diluted with a sterilized saline to get a suspension of $10^6$–$10^7$ cells/ml. One ml of the diluted suspension is smeared on a commercial MRS medium containing 1.5% agar and incubated at 37° C. for two days or longer. The grown colonies were harvested and inoculated to MRS medium and incubated at 37° C. for one day to get the aimed strain.

The composition of MRS medium is shown below.

| | |
|---|---|
| Peptone | 10 (g/L) |
| Meat extract | 5 |
| Yeast extract | 5 |
| Glucose | 20 |
| Dipotassium hydrogenphosphate | 2 |
| Tween 80 | 1 |
| Diammonium hydrogen citrate | 2 |
| Sodium acetate | 5 |
| Magnesium sulfate | 0.1 |
| Manganese sulfate | 0.05 |

The microbial characteristics of the strain are shown below.

A Morphological properties

| | |
|---|---|
| (1) Shape of cells: | Rods |
| (2) Motility: | No |

| | -continued | |
|---|---|---|
| (3) Spore formation: | | No |
| (4) Gram staining: | | Positive |
| B Growth on a medium | | |
| (1) Growth at 15° C.: | | No growth |
| (2) Growth at 45° C.: | | Growth |
| C Physiological properties | | |
| (1) Catalase: | | Negative |
| (2) No gas formation from glucose. | | |
| (3) No gas formation from gluconic acid. | | |
| (4) Production of DL-lactic acid by lactic acid fermentation of glucose. | | |
| (5) Acid produced from. | | |
| 1. Ribose | | – |
| 2. Arabinose | | – |
| 3. Xylose | | – |
| 4. Rhamnose | | – |
| 5. Mannitol | | – |
| 6. Sorbitol | | – |
| 7. Ribitol | | – |
| 8. Glycerol | | – |
| 9. Fructose | | – |
| 10. Mannose | | + |
| 11. Galactose | | + |
| 12. Glucose | | + |
| 13. Lactose | | + |
| 14. Maltose | | – |
| 15. Sucrose | | – |
| 16. Trehalose | | – |
| 17. Cellobiose | | – |
| 18. Raffinose | | – |
| 19. Melibiose | | – |
| 20. Melezitose | | – |
| 21. Salicin | | – |
| 22. Gluconate | | – |

(+ and – indicate positive and negative, respectively.)

The microbial characteristics are searched in consideration of descriptions in Bergey's Manual of Systematic Bacteriology, Vol.2, pp. 1222–1224 (1986). The obtained strain was identified as *Lactobacillus helveticus* and deposited in National Institute of Bioscience and Human-Technology (NIBH), Agency of Industrial Science and Technology as *Lactobacillus helveticus* SBT 2171 (FERM BP-5445 which was transferred from FERM P-14381).

The crude enzyme solution is obtained by harvest of cells from culture, disruption of the harvested cells by conventional methods such as enzymatic treatment for example lysozyme, mechanical treatment for example ultrasonication, lyophilization, ball mill treatment and French press, and chemical treatment using an organic solvent, and removal of disrupted cells to get the aimed supernatant, crude enzyme solution.

Furthermore, conventional methods such as various chromatographies, salting out, electrophoresis and immunoblotting methods used for purification of proteolytic enzymes can be applied to purification of the enzyme from the resultant crude enzyme solution. For the purification of the endopeptidase of the present invention, these purification methods can be used at any stage of the purification steps.

The obtained endopeptidase has aforementioned characteristics.

The endopeptidase of the present invention can be used in any form such as crude or purified enzyme solution or isolated endopeptidase.

The endopeptidase of the present invention can be used together with a proteinase and an aminopeptidase for the hydrolysis of proteins and peptides used as raw materials of foods, drinks, feeds, cosmetics and medicines. In addition, the characteristics of the endopeptidase of the present invention which hydrolyzes peptides but not proteins can be used for selective production of specific peptides. Furthermore, since the endopeptidase of the present invention is an enzyme produced by dairy lactic acid bacteria, it can be safely used.

For example, the endopeptidase can be added to raw materials for the production process of cheeses, proteins or peptides together with an aminopeptidase to effectively reduce bitter taste and improve flavors of products. In addition, the endopeptidase of the present invention can be used together with a proteinase and/or peptidase with high substrate specificity to control the chain length of aimed peptides to 2–10 amino acids. Therefore, the endopeptidase of the present invention can be favorably used for the production of hydrolyzates of proteins and peptides which are used as raw materials of foods, drinks and medicines.

The present invention will be explained in detail by the examples shown below.

[EXAMPLE 1]

In 10 bottles each containing one liter of a modified MRS medium mentioned below, 10 L in total, *Lactobacillus helveticus* SBT 2171 (FERM BP-5445) was inoculated and cultured statically at 37° C. overnight, for 10–16 hrs. The cultured cells were harvested by centrifugation at 7,500×G, for 10 min. and at 4° C., at late-logarithmic phase when the culture showed turbidity of 1.0 determined at 650 nm using a cell of one cm length. The harvested cells were washed twice with each 100 ml of 50 mM 4-(2-hydroxyethyl)-1-piperazine-ethanesulfonic acid (HEPES) buffer, pH 7.0, containing 15 mM calcium chloride, then suspended in 120 ml of the same buffer. The cell suspensions each having 60 ml volume were cooled with a coolant at −10° C. and disrupted by ultrasonication with a power of 10 intensity, pulse 20%, only 0.2 sec. output in one sec., for 40 min. The turbidity of the suspension became 20% or less in comparison to that of prior the ultrasonication. Then, the disrupted cells were centrifuged at 30,000×G, for 10 min. and at 4° C., and the resultant supernatant was used as a crude enzyme solution. The amount of the protein in the crude enzyme solution obtained from 10 L of culture was 10.3 g as bovine serum albumin.

The composition of the modified MRS medium is shown below.

| Peptone | 10 (g/L) |
|---|---|
| Meat extract | 5 |
| Yeast extract | 5 |
| Glucose | 20 |
| β-Glycerophosphoric acid | 2 |
| Tween 80 | 1 |
| Triammonium citrate | 2 |
| Sodium acetate | 3 |
| Magnesium chloride | 0.1 |
| Calcium chloride | 2.2 |

[EXAMPLE 2]

The following columns were equipped on Fast Protein Liquid Chromatography (Pharmacia) and 70 ml of the crude enzyme solution obtained from Example 1 and containing 991 mg of protein as bovine serum albumin was applied and purified by the following procedure. All purification steps were carried out at 4° C. and the samples used were filtered with a filter having pore size of 0.22 μm. The amount of protein was estimated by absorbance at 280 or 214 nm. The enzyme activity during the purification steps was determined with a sample solution composed of 200 μl of a substrate solution of 0.5 mM MeO-Suc-Arg-Pro-Tyr-pNA dissolved in 50 mM HEPES, pH 7.0, with five μl of the test enzyme solution and a commercial leucine aminopeptidase. The reaction mixture was incubated at 30° C. for 15 min. and the absorbance at 405 nm was determined with Microplate Reader Model 3550-UV (Bio-Rad Laboratories). In the case of the characteristics of the enzyme and precise measurement of the enzyme activity at each purification step, a reversed phase chromatography were used which linearly increases the concentration of acetonitrile from 0 to 40% in 0.1% trifluoroacetic acid, and the hydrolysis rate of Tyr-Gly-Gly-Phe-Met (SEQ ID NO: 2) or the production rate of Tyr-Gly-Gly from Tyr-Gly-Gly-Phe-Met (SEQ ID NO: 2) were determined.

Q-Sepharose chromatography

Q-Sepharose HP 26/10 column (Pharmacia) was equilibrated with 20 mM Tris-HCl buffer, pH 8.0, and the crude enzyme solution was applied. Then, concentration of sodium chloride in the buffer was linearly increased from zero to one M to elute the fractions with the activity at a flow rate of 2.0 ml/min. The eluent was fractionated at four ml each and the resultant fractions with the activity were pooled and stored at −50° C. until use.

Phenyl-Sepharose chromatography

A total of 3.4 M ammonium sulfate solution was added dropwise to the pooled fractions obtained in the Q-Sepharose chromatography to get a sample solution with final concentration of 1.7 M ammonium sulfate. Phenyl Sepharose HP 26/10 column (Pharmacia) was equilibrated with 20 mM Tris-HCl buffer containing 1.7 M ammonium sulfate, pH 7.5, and the prepared crude enzyme solution was applied. Then, concentration of ammonium sulfate in the buffer was linearly decreased to elute fractions with activity at a flow rate of 2.0 ml/min.. The eluent was fractionated at four ml each. The fractions with activity were pooled, desalted and concentrated with an ultrafiltration membrane which molecular weight cut-off is 10,000. The resultant solution was frozen and kept at −50° C. until use.

Mono-Q-chromatography

Mono-Q 5/5 column (Pharmacia) was equilibrated with 20 mM Tris-HCl buffer, pH 7.5, and the pooled fraction obtained by Phenyl Sepharose chromatography was applied. Then, concentration of sodium chloride in the buffer was linearly increased from zero to one M to elute the fractions with activity at a flow rate of 0.5 ml/min. The fraction size was at 0.5 ml each. The resultant active fractions were desalted and concentrated with an ultrafiltration membrane which molecular weight cut-off is 10,000. The resultant solution was stored at −50° C. until use.

Hydroxylapatite chromatography

Hydroxylapatite Superformance 5/7.5 column (Merck) was equilibrated with 5 mM potassium phosphate buffer, pH 7.0, and the pooled fractions obtained by Mono-Q chromatography was applied. Then, concentration of a potassium phosphate buffer, pH 7.0, was linearly increased from five to 500 mM to elute the fractions with activity at a flow rate of 0.25 ml/min. The eluent was fractionated at 0.5 ml each and the resultant active fractions were desalted and concentrated with an ultrafiltration membrane which molecular weight cut-off is 10,000. The resultant fractions were frozen and kept at −50° C. until use.

By carrying out the above mentioned procedures, 0.32 mg of the purified enzyme of the present invention showing a single band in SDS polyacrylamide gel electrophoresis was obtained with a yield of 3.1%.

The yield and specific activity of the enzyme in each purification steps are shown in Table 1.

TABLE 1

| Purification step | Total protein (mg) | Total activity (μmol/min.) | Specific activity (μmol/min./mg) | Yield (%) | Purification (fold) |
|---|---|---|---|---|---|
| a. Extract Chromatography | 991 | 922 | 0.9 | 100 | 1 |
| b. Q-Sepharose | 58.2 | 323 | 6 | 35 | 6 |
| c. Phenyl Sepharose | 6.0 | 161 | 27 | 17 | 29 |
| d. Mono-Q- | 0.97 | 58.4 | 60 | 6.3 | 65 |
| e. Hydroxylapatite | 0.32 | 28.8 | 89 | 3.1 | 96 |

[Test example 1]

Purity at each purification step shown in Table 1 of Example 2 was confirmed by SDS polyacrylamide gel electrophoresis according to the method of Laemmli [Nature, vol. 227, pp. 680–685 (1979)]. The results are shown in FIG. 1. In FIG. 1, a–e represent the purification steps in Table 1, and f represents markers (phosphorylase b 97.4 kDa, bovine serum albumin 66.2 kDa and ovalbumin 45 kDa).

The endopeptidase of the present invention after Hydroxylapatite chromatography was stained at a slightly higher site than that of bovine serum albumin having molecular weight of 66.0 kDa, exhibiting a clear single band of about 70 kDa.

[Test example 2]

The isoelectric point of purified endopeptidase obtained by Example 2 was determined by isoelectric focusing. Automatic electrophoresis apparatus Phast System, PhastGel IEF 3–9 and PhastGel IEF 4–6.5 (all items are products of Pharmacia) were used and the purified endopeptidase was migrated with markers. The protein in gel after electrophoresis was automatically stained with silver in the above mentioned apparatus to detect the sample. The isoelectric point of the endopeptidase of the present invention was determined as 4.8.

[Test example 3]

Figure 2:
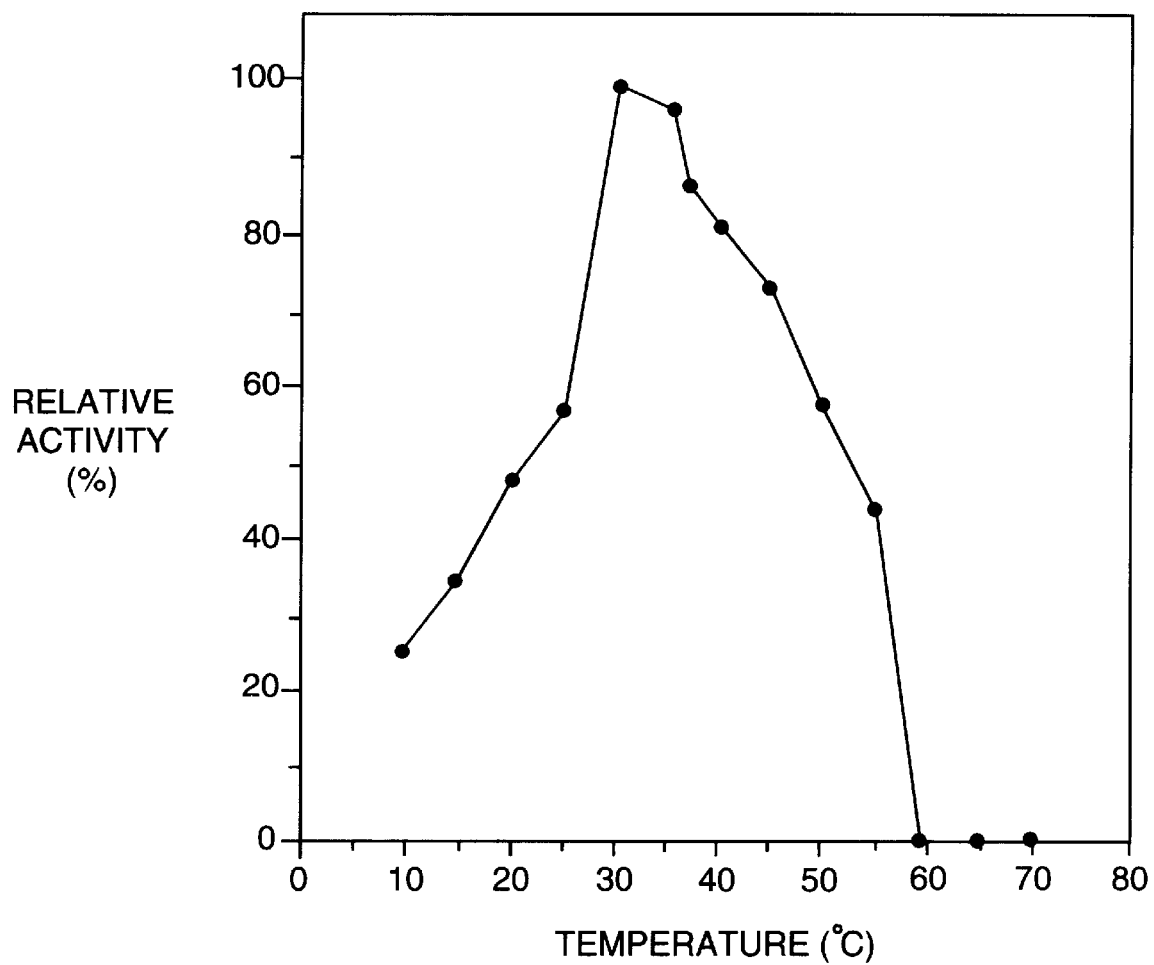
FIG. 2 shows the temperature dependency of the activity of the endopeptidase of the present invention.

The temperature dependency of the activity of the endopeptidase of the present invention was determined using Tyr-Gly-Gly-Phe-Met (SEQ ID NO: 2) as a substrate at pH 7.0 and at a temperature range of 10–70° C. An enzyme solution prepared by addition of 10 μl of the purified endopeptidase at a concentration of five μg/ml to 70 μl of 50 mM HEPES buffer, pH 7.0, was pre-incubated for five min.. Then, 20 μl of 10 mM Tyr-Gly-Gly-Phe-Met (SEQ ID NO: 2) was added and incubated for 20 min. and the reaction was stopped by addition of 50 μl of 30% acetic acid. The determination of the activity was carried out by reversed phase chromatography according to the method shown in Example 2. The results are shown in FIG. 2. The activity of endopeptidase of the present invention reached maximum at 30° C. and 70% of maximum activity was still remained in a temperature range of 30–45° C.

[Test example 4]

Figure 3:
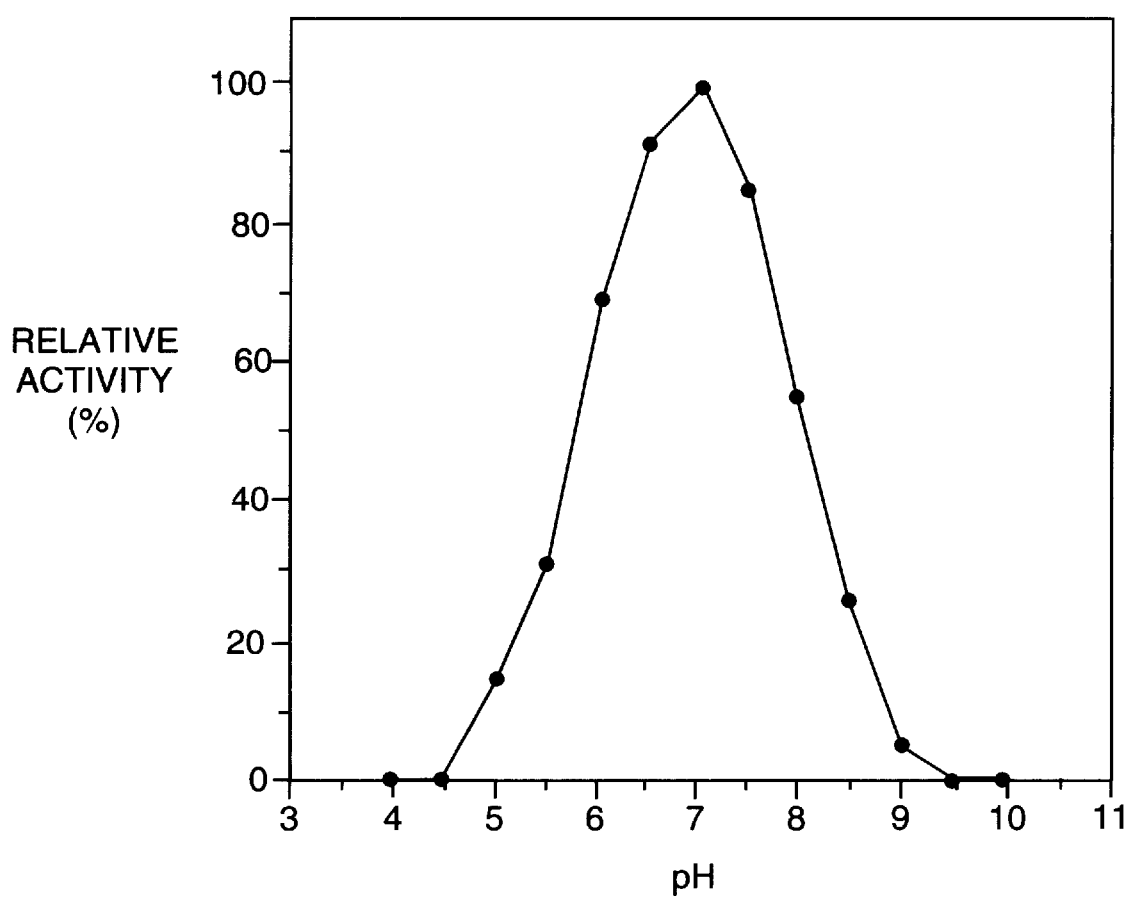
FIG. 3 shows the pH dependency of the activity of the endopeptidase of the present invention.

The pH dependency of the activity of the endopeptidase of the present invention was determined using Tyr-Gly-Gly-Phe-Met (SEQ ID NO: 2) as a substrate at a range of pH 4–10 at 30° C. Enzyme solutions were prepared by addition of each 10 μl of the purified endopeptidase at a concentration of 5 μg/ml to 70 μl of buffer solutions with different pHs, which contained 20 mM of malic acid, MES, HEPES and boric acid, at different ratios. Each of the enzyme solutions was pre-incubated at 30° C. for 5 min., and then added with 20 μl of 10 mM Try-Gly-Gly-Phe-Met (SEQ ID NO: 2) and, incubated for 20 min.. The reaction was stopped by addition of 50 μl of 30% acetic acid. The measurement of the activity was carried out by reverse phase chromatography according to the method shown in Example 2. The results are shown in FIG. 3. The maximum activity of endopeptidase of the present invention was observed at about pH 7 and the activity was hardly found in an acidic range at pH 4.5 or lower or in an alkaline range at pH 9.0 or higher.

[Test example 5]

Figure 4:
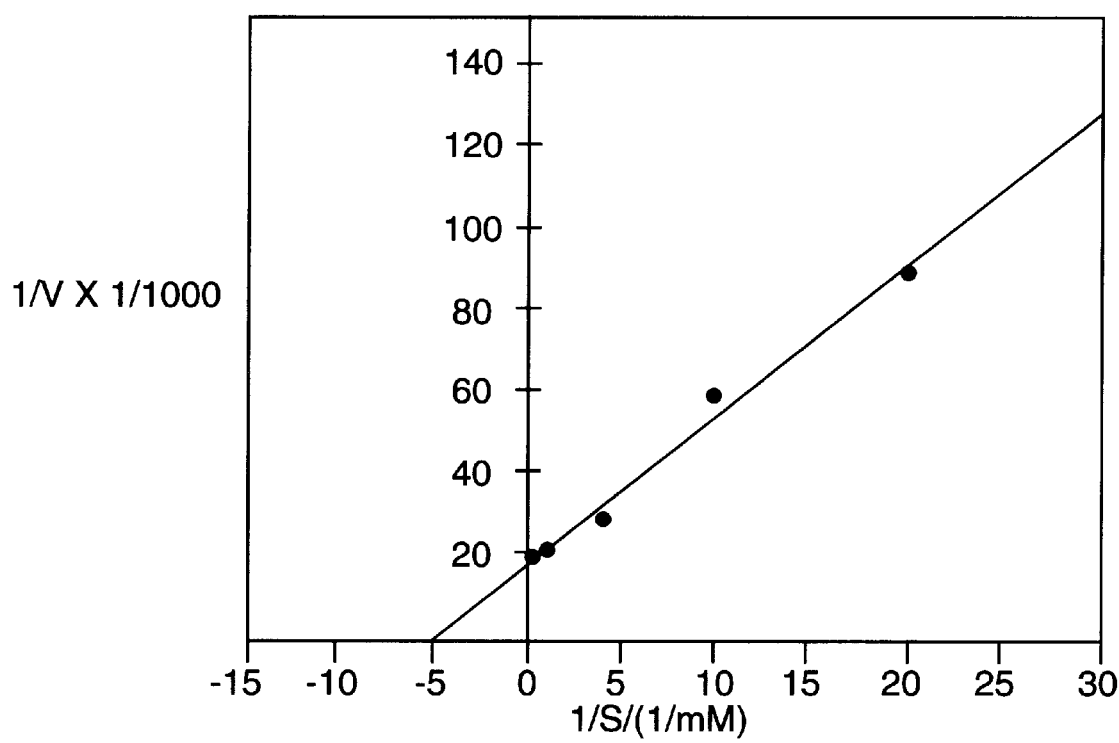
FIG. 4 shows the Lineweaver-Burk plot expressing the Michaelis constant ($K_m$ value) and the maximum velocity ($V_{max}$ value) of an enzyme reaction of the endopeptidase of the present invention using Tyr-Gly-Gly-Phe-Met (SEQ ID NO: 2) as a substrate.

The maximum velocity ($V_{max}$ value) and Michaelis constant ($K_m$ value) of the endopeptidase of the present invention to Tyr-Gly-Gly-Phe-Met (SEQ ID NO: 2) were determined. An enzyme solution prepared by addition of 10 μl of the purified endopeptidase at a concentration of five μg/ml to 70 μl of 50 mM HEPES buffer, pH 7.0, was pre-incubated for five min. at 30° C. Then, 20 μl of different concentrations of Tyr-Gly-Gly-Phe-Met (SEQ ID NO: 2) was added and incubated for 20 min. and the reaction was stopped by addition of 50 μl of 30% acetic acid. The measurement of the activity was carried out by reversed phase chromatography method according to that in Example 2. The obtained results were used to prepare Line-weaver-Burk plot. The results are shown in FIG. 4 indicating $K_m$ value of 0.20 mM and $V_{max}$ value of 56 μmol/min./mg.

[Test example 6]

The substrate specificity of the endopeptidase of the present invention was determined. In 200 μl of 2 to 5 mM substrate in 50 mM HEPES buffer, pH 7.0, 10 μl of the endopeptidase solution of the present invention in 50 mM HEPES buffer, pH 7.0, at five μg/ml was added and incubated at 30° C. for 5.0 hrs. Then, the reaction mixture was applied to reversed phase chromatography and eluted using linear increase of concentration of acetonitrile in 0.1% trifluoroacetic acid from zero to 60%. The hydrolysis was determined from the decrease of the peak area of the substrate and/or the appearance of a new peak(s) at 214 nm on the chromatogram.

The results are shown in Table 2.

TABLE 2

| Substrate | Hydrolysis | Substrate | Hydrolysis |
|---|---|---|---|
| Leu-Leu | − | Dynorphin A, f1–6 (6) | + |
| Phe-Met | − | Dynorphin A, f1–8 (8) | + |
| Phe-Val | − | Dynorphin A, f1–10 (10) | + |
| Pro-Ala | − | Dynorphin A, f1–13 (13) | + |
| Ala-Pro | − | Dynorphin A, (17) | + |
|  |  | Parathyroid hormone, human, f13–34 (22) | + |
|  |  | Parathyroid hormone, human, f1–34 (34) | + |
|  |  | Parathyroid hormone, human, f1–38 (38) | − |
|  |  | Parathyroid hormone, human, f1–44 (44) | − |
| Leu-Leu-Leu | + | β-Casein, f108–113 (6) | + |
| Leu-Gly-Gly | − | β-Casein, f177–183 (7) | − |
| Met-Gly-Gly | − | β-Casein, f203–209 (7) | + |
| Tyr-Gly-Gly | − |  |  |
| Pro-Gly-Gly | − | $α_{s1}$-Casein | − |
|  |  | β-Casein | − |
| Ala-Ala-Ala-Ala (SEQ ID NO:3) | + | κ-Casein | − |
| Gly-Pro-Gly-Gly | − |  |  |

TABLE 2-continued

| Substrate | Hydrolysis | Substrate | Hydrolysis |
|---|---|---|---|
| (SEQ ID NO:4) |  |  |  |
| Gly-Pro-Arg-Pro (SEQ ID NO:5) | − | Lys-pNA | − |
| Pro-Lys-Gly-Gly (SEQ ID NO:6) | − | Pro-pNA | − |
|  |  | Ala-Pro-pNA | − |
| Ala-Ala-Ala-Ala-Ala (SEQ ID NO:7) | + | Z-Phe-Ala | − |
| Met-Enkephalin (5) | + | Suc-Phe-pNA | − |
| Pro-Gly-Lys-Ala-Arg (SEQ ID NO:8) | − | Bzl-Cys-pNA | − |
|  |  | Suc-Ala-Ala-Pro-Leu-pNA (SEQ ID NO:10) | − |
| Ala-Ala-Ala-Ala-Ala-Ala (SEQ ID NO:9) | + | MeO-Suc-Arg-Pro-Tyr-pNA | − |
| β-Casomorphin (7) | − | MeO-Suc-Arg-Pro-Tyr-pNA + LAP* | + |
| Bradykinin (9) | + |  |  |
| Angiotensin (10) | + |  |  |
| Substance P (11) | + |  |  |
| Neurotensin (13) | + |  |  |
| Insulin β-chain (30) | + |  |  |

LAP* represents a leucine aminopeptidase.
Numerals in ( ) represent number of amino acid residues,
+ represents that a substrate was hydrolyzed
− represents that a substrate was not hydrolyzed.

Table 2 shows that the endopeptidase of the present invention can hydrolyzes peptides of 3 to 34 amino acid residues but not proteins such as caseins within the tested substrates in Test example 6.

[Test example 7]

The influences of enzyme inhibitors on the-activity of the endopeptidase of the present invention was determined. The purified endopeptidase (0.5 μg protein/ml) in 40 mM HEPES, pH7.0, was incubated for 30 min. at 4° C. with 0.001 to 2.0 mM enzyme inhibitors. After pre-incubating the enzyme mixture for 5 min. at 30° C., 1 mM Tyr-Gly-Gly-Phe-Met (SEQ ID NO: 2) was added to start the reaction and the mixture was incubated for 20 min. at 30° C. The reaction was stopped by 10% acetic acid.

The enzyme activity was determined by reversed phase chromatography. The results showed inhibition by 1,10-phenanthroline, ethylenediaminetetraacetic acid (EDTA), and p-chloromercuribenzenesulfonic acid (p-CMBS) as described earlier. However, no inhibition was found by phenylmethylsulfonyl fluoride (p-CMBS) or iodoacetic acid.

[Test example 8]

The influences of metal ions to the activity of the endopeptidase of the present invention was determined similarly by the method according to Test example 7. The enzyme activity was inhibited by $Cu^{2+}$, $Zn^{2+}$ and $Fe^{2+}$.

[Test example 9]

The purified endopeptidase obtained by Example 2 was investigated with Amino Acid Sequencer Model 476A (Applied Biosystems) and an N-terminal amino acid sequence of Val-Arg-Gly-Gly-Ala-Gly-Asp-Ile-Thr-Glu-Ala-Asp-Leu-Ser-Ala-Arg-Pro-Gln-Asp-Asn-Leu-Tyr-Leu-Ala-Val-Asn- shown as (SEQ ID NO: 1).

We claim:

1. An isolated endopeptidase produced by *Lactobacillus helveticus* and comprising the following properties:
   (a) a molecular weight of about 70 kDa, as determined by SDS polyacrylamide electrophoresis;
   (b) an isoelectric point of about 4.8;
   (c) optimal activity at a temperature of about 30° C.;
   (d) optimal activity at a pH of about 7.0;
   (e) substrate specificity wherein said endopeptidase hydrolyzes internal peptide bonds of peptides but not internal peptide bonds in proteins;
   (f) its activity is inhibited by 1,10-phenanthroline, ethylenediaminetetraacetic acid (EDTA), and p-chloromercuribenzenesulfonic acid (p-CMBS); and
   (g) its activity is inhibited by $Cu^{2+}$, $Zn^{2+}$ and $Fe^{2+}$.

2. The isolated endopeptidase of claim 1 wherein said peptides are about 3–34 amino acids in length.

3. The endopeptidase of claim 1 wherein said *Lactobacillus helveticus* is *Lactobacillus heleveticus* SBT 2171 (FERM BP-545).

4. The endopeptidase of claim 1 which activity shows a Michaelis constant (Km value) of about 0.20 mM and a maximum velocity (V max value) of about 56 μmol/min/mg.

5. The endopeptidase of claim 1 wherein an amino acid sequence in the N-terminus is Val-Arg-Gly-Gly-Ala-Gly-Asp-Ile-Thr-Glu-Ala-Asp-Leu-Ser-Ala-Arg-Pro-Gln-Asp-Asn-Leu-Tyr-Leu-Ala-Val-Asn- shown in SEQ ID NO:1.

* * * * *